(12) United States Patent
Ross, Jr.

(10) Patent No.: US 9,078,478 B2
(45) Date of Patent: Jul. 14, 2015

(54) THERAPEUTIC SLEEVE DEVICE

(75) Inventor: Johnny Ross, Jr., Mansfield, TX (US)

(73) Assignee: Medlab, LLC, Mansfield, TX (US)

( * ) Notice: Subject to any disclaimer, the term of this patent is extended or adjusted under 35 U.S.C. 154(b) by 445 days.

(21) Appl. No.: 13/544,144

(22) Filed: Jul. 9, 2012

(65) Prior Publication Data
US 2014/0012161 A1  Jan. 9, 2014

(51) Int. Cl.
*A61B 5/11* (2006.01)
*A41D 27/10* (2006.01)
*A61B 5/00* (2006.01)
*A41D 1/00* (2006.01)

(52) U.S. Cl.
CPC ............. *A41D 27/10* (2013.01); *A41D 1/002* (2013.01); *A61B 5/1114* (2013.01); *A61B 5/6804* (2013.01); *A61B 5/6806* (2013.01); *A61B 2505/09* (2013.01); *A61B 2562/0219* (2013.01); *A61B 2562/046* (2013.01)

(58) Field of Classification Search
CPC ........ A61B 5/11; A61B 5/112; A61B 5/1126; A61B 5/4528; A61B 5/6804; A61B 17/1739; A61B 2019/5248
See application file for complete search history.

(56) References Cited

U.S. PATENT DOCUMENTS

| | | | |
|---|---|---|---|
| 4,016,868 A * | 4/1977 | Allison | 600/388 |
| 5,980,472 A | 11/1999 | Seyl | |
| 6,059,576 A | 5/2000 | Brann | |
| 6,275,996 B1 * | 8/2001 | Redwood et al. | 2/160 |
| 7,559,902 B2 * | 7/2009 | Ting et al. | 600/529 |
| 7,634,379 B2 | 12/2009 | Noble | |
| 7,640,804 B2 | 1/2010 | Daumer | |
| 7,712,365 B1 | 5/2010 | James | |
| 7,981,057 B2 * | 7/2011 | Stewart | 600/595 |
| 8,188,868 B2 * | 5/2012 | Case, Jr. | 340/573.1 |
| 8,348,865 B2 * | 1/2013 | Jeong et al. | 600/595 |
| 8,674,810 B2 * | 3/2014 | Uysal et al. | 340/10.4 |
| 8,840,548 B2 * | 9/2014 | Mazzarolo | 600/301 |
| 8,961,439 B2 * | 2/2015 | Yang et al. | 600/595 |
| 2006/0122528 A1 | 6/2006 | Gal | |
| 2007/0032748 A1 | 2/2007 | McNeil | |
| 2007/0285868 A1 | 12/2007 | Lindberg | |
| 2008/0218310 A1 | 9/2008 | Alten | |
| 2010/0312297 A1 | 12/2010 | Volpe | |
| 2011/0113713 A1 | 5/2011 | Lui et al. | |
| 2011/0137138 A1 | 6/2011 | Johansson | |
| 2013/0021152 A1 | 1/2013 | Vock | |

FOREIGN PATENT DOCUMENTS

| | | |
|---|---|---|
| JP | 2010507398 | 3/2010 |
| WO | WO 0110508 | 2/2001 |
| WO | WO2009112281 | 9/2009 |

* cited by examiner

*Primary Examiner* — Max Hindenburg
(74) *Attorney, Agent, or Firm* — Eric Karich; Karich & Associates (57) ABSTRACT

A therapeutic sleeve device apparatus has a flexible sleeve shaped to be worn around the arm of the user. The device has an array of accelerometers disposed on or within the flexible sleeve to physically associate with positions on the arm of the user. Each array of accelerometers has a sample rate that can be configured for sensing body movement during a movement activity. A power source and a data collection system are operably connected to the array of accelerometers. The data collection system has a means for receiving data from the array of accelerometers and processing that data into a storable format.

17 Claims, 8 Drawing Sheets

THERAPEUTIC SLEEVE DEVICE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates generally to therapeutic device, and more particularly to a therapeutic sleeve device for assisting a patient with physical rehabilitation of an arm or shoulder injury.

2. Description of Related Art

The following art defines the present state of this field:

Granville et al., WO 01/10508, teaches a position sensor device, which is attachable to a user and is able to indicate the position and/or motion of a body part of the user, for physical rehabilitation of injured limbs. The device includes a sleeve (e.g., glove, sock, armband, ring, bracelet, legband, anklet) that includes a sensor such as an accelerometer, gyroscope, potentiometer, or similar sensor. The sleeve preferably includes an accelerometer on the thigh and one on the ankle, and also an angle sensor at the knee. In one embodiment, the device includes an accelerometer at the ankle and one at the elbow. In another, the device is incorporated into a sock, and further includes pressure sensors.

Harms et al., WO 2009/112281, teaches various forms of "smart textiles" for "posture classification" (i.e., orientation and movement of at least one body segment, preferably to detect changes in posture, body movements, and various physical activities). It preferably includes a loose fitting garment (e.g., long sleeve shirt) that includes an apparatus for detection of the orientation of at least one body segment integrated to the garment. The garment includes a plurality of sensing terminals and at least one processing unit in communication with the terminals. The sensors discussed in this reference may include accelerometers, gyroscopes, pressure sensors, and a range of alternative sensors. The sensors are not placed with precision, but depend upon various discussed methods to attempt to track movements with acceptable precision despite the variable movement of the garment. Placement of the various sensors is different than in the subject invention.

Brann, U.S. Pat. No. 6,059,576, teaches a movement sensor device and method to monitor and train an individual on proper motion during physical activities, such as work. The system employs an electronic device which tracks and monitors an individual's motion through the use of an accelerometer capable of measuring parameters associated with the individual's movement. The device also employs a user-programmable microprocessor which receives, interprets, stores and responds to data relating to the movement parameters. The downloadable, self-contained device can be worn at various positions along the torso or appendages being monitored depending on the specific physical task being performed. The device also detects the speed of movements made while the device is being worn. When a pre-programmed recordable event is recognized, the device records the time and date of the occurrence while providing feedback to the wearer via visual, audible and/or tactile warnings.

Seyl, U.S. Pat. No. 5,980,472, teaches a joint movement monitoring system that includes a carrier configured for wearing by a user around a wrist (arm band, glove, etc.). The system includes a plurality of position sensors coupled with the carrier for sensing various hand positions of the subject. The preferred carrier is in the form of an elastic wrist band that encompasses the wrist and adjacent portions of the hand and forearm without covering any portions of the subject's fingers. The preferred sensors include Hall effect sensors mounted to the carrier on the forearm side of the wrist.

Gal, U.S. 2006/0122528, teaches clothing that includes various sensors for monitoring movements of a user. The sensors are sensitive to expansion and contractions of underlying regions of a monitored subject.

Johansson et al., U.S. 2011/0137138, teaches a portable apparatus for managing a plurality of events related to a patient and for recording and storing input data related to said events is disclosed. The apparatus includes a sensor to record measurements related to a motion exercise. Further, a storage unit is arranged to retrievably store patient input data and measurements to enable diagnosing a neurological disease.

J.P. 2010507398 (Japanese reference), teaches a limb movement monitoring system that includes a motion sensor operably mounted in a garment.

The above-described references are hereby incorporated by reference in full.

SUMMARY OF THE INVENTION

The present invention teaches certain benefits in construction and use which give rise to the objectives described below.

The present invention provides a therapeutic sleeve device for tracking and recording movement data of an arm of a user, and also for providing treatment to the arm. The therapeutic sleeve device includes a flexible sleeve shaped to be worn around the arm and shoulder of the user. The device has an array of accelerometers disposed on or within the flexible sleeve to physically associate with positions on the arm of the user. Each array of accelerometers has a sample rate that can be configured for sensing body movement during a movement activity. A power source and a data collection system are operably connected to the array of accelerometers. The data collection system has a means for receiving data from the array of accelerometers and processing that data into a storable format.

A primary objective of the present invention is to provide a therapeutic sleeve device having advantages not taught by the prior art.

Another objective is to provide a therapeutic sleeve device that can collect movement data and transmit this information to a computer device, to be stored and analyzed.

A further objective is to provide a therapeutic sleeve device that collects detailed information about the particular orientation and movement of many strategic points of the user's upper extremities, to more accurately track the user's movements to ensure activities, such as physical rehabilitation, are performed correctly.

A further objective is to provide a therapeutic sleeve device that has the capability to heat and cool the user's upper extremities, as deemed therapeutically appropriate by a clinician.

A further objective is to provide a therapeutic sleeve device that administers various forms of additional treatments in conjunction with physical rehabilitation exercises.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

The above-described drawing figures illustrate the invention, a therapeutic sleeve device 10 for tracking and recording movement data of an arm 14 of a user 12, and also for providing treatment to the arm 14.

Figure 1:
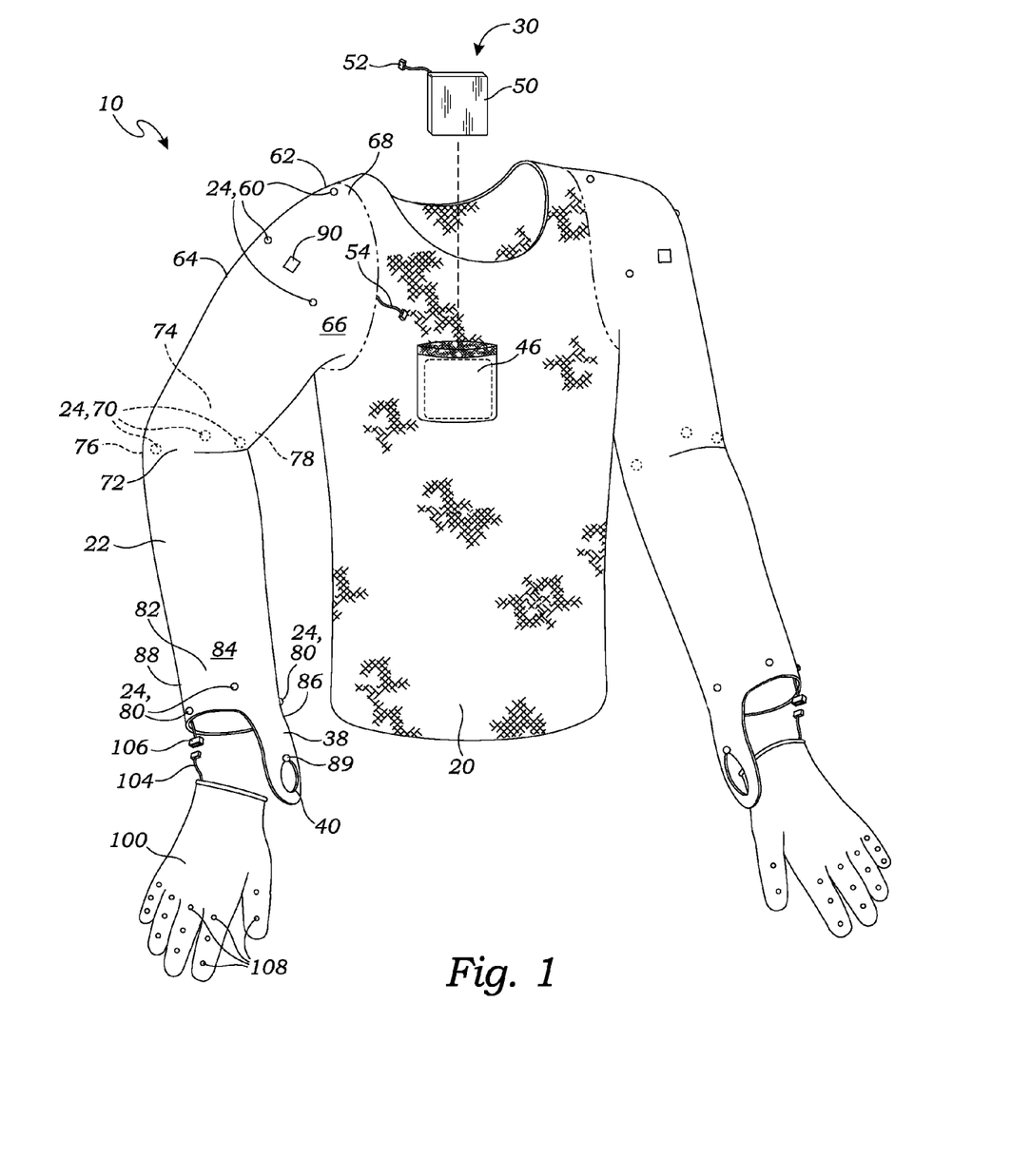
FIG. 1 is an exploded perspective view of a therapeutic sleeve device according to one embodiment of the present invention, illustrating a data collector used in one embodiment of a data collection system.
Figure 2:
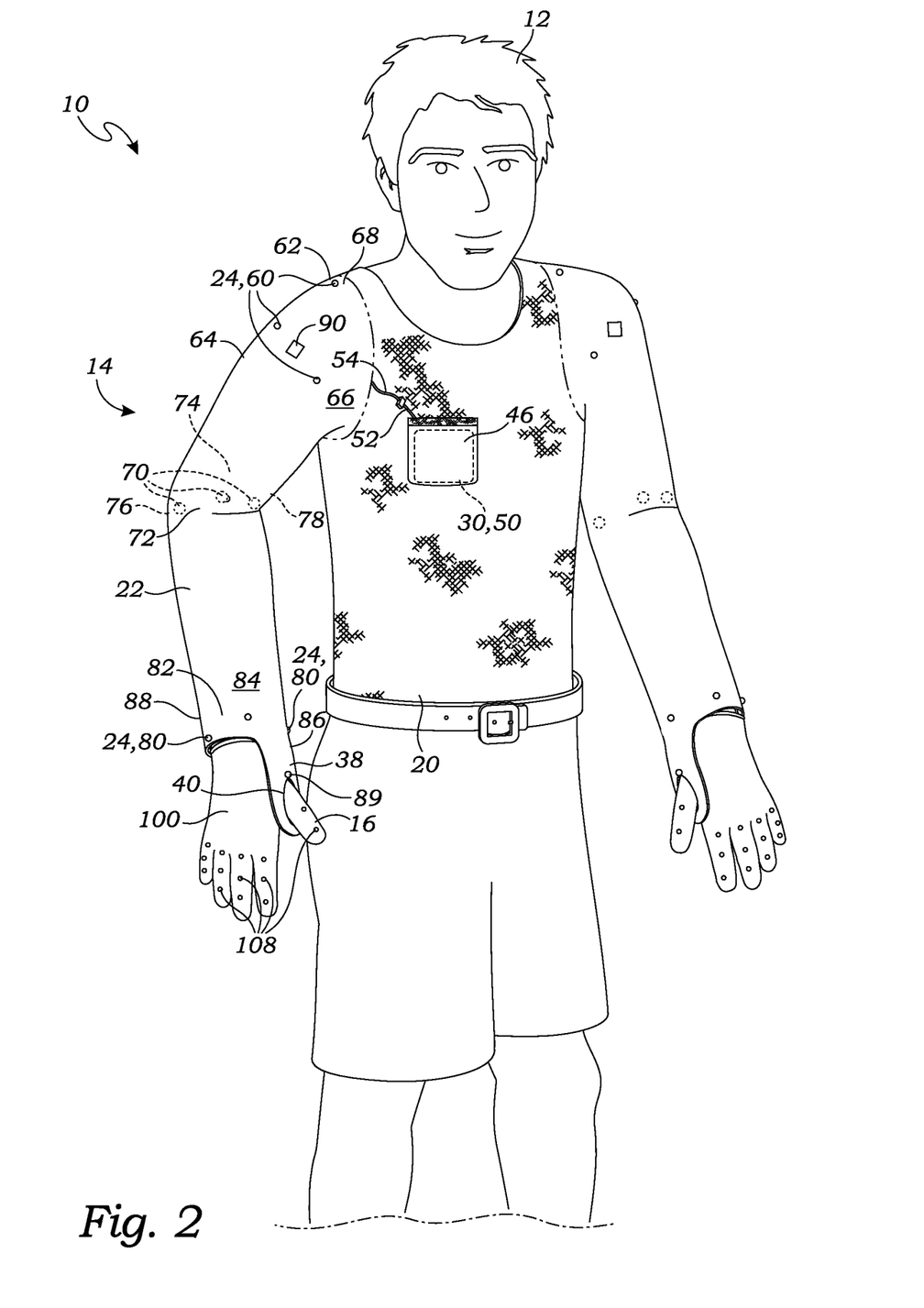
FIG. 2 is a perspective view of a user wearing the therapeutic sleeve device of FIG. 1.

FIG. 1 is an exploded perspective view of one embodiment of the therapeutic sleeve device 10. FIG. 2 is a perspective view of a user 12 wearing the therapeutic sleeve device 10 of FIG. 1. As shown in FIGS. 1 and 2, the therapeutic sleeve device 10 includes at least one flexible sleeve 22 having an array of accelerometers 24, and a data collection system 30 for collecting data from the accelerometers 24.

The therapeutic sleeve device 10 may include a single flexible sleeve 22 in the simplest embodiment; or a pair of the flexible sleeves 22 for generating movement data for both of the user's arms 14. In the embodiment of FIGS. 1 and 2, the therapeutic sleeve device 10 includes a shirt body 20 that is shaped for covering an abdomen of a user 12. The shirt body 20 may be constructed of an suitable fabric or similar material that is suitable for clothing. In this embodiment, the flexible sleeves 22 may be compression sleeves. As illustrated in FIGS. 1 and 2, the compression sleeves 22 may extend from the shirt body 20 to a distal end 38 having a thumbhole 40 for receiving the user's thumb 16 therethrough and correctly position the flexible sleeve 22 on the arm 14. The thumbhole 40 may therefore engage the user's thumb 16 to secure the sleeve 22 to the user 12 and minimize extraneous movement of the flexible sleeve 22. However, while one embodiment of the flexible sleeve 22 is illustrated, the particular shape and form of the flexible sleeve 22 may vary according to the design of one skilled in the art.

The therapeutic shirt 20 may also include a pocket 46 on the shirt body 20 (or otherwise associated with the user and/or the flexible sleeve 22) in which portions of the data collection system 30 may be positioned. In this embodiment, a data collector 50 having a suitable housing is shaped to be positioned in the pocket 46.

The data collection system 30, described in greater detail below, may be operably engaged with the various sensors of the flexible sleeve 22. In some of the embodiments described below, this may be wireless. In the illustrated embodiment, a first electrical connection 52 (cable) of the data collector 50 may be removably connected with a second electrical connection 54 of the flexible sleeve 22, to operably connect the data collector 50 with the array of accelerometers 24 and other components. Such a connection allows the array of accelerometers 24 to transmit data to the data collector 50 in the pocket 46 of the shirt body 20.

As illustrated in FIGS. 1 and 2, the array of accelerometers 24 is disposed on or within each of the flexible sleeves 22 to physically associate with positions on the arm(s) 14 of the user 12. The disposition of the array of accelerometers 24 is discussed in greater detail below. Each of the array of accelerometers 24 may have a sample rate that can be configured for sensing body movement during a movement activity. Each of the accelerometers 24 may be selected from various accelerometers or equivalent devices that are known in the art. Since the construction of accelerometers is known in the art, they are not described in greater detail herein.

As illustrated in FIGS. 1 and 2, the array of accelerometers 24 includes at least one shoulder accelerometer 60 that may be mounted in a shoulder area 62 of the flexible sleeve 22. The shoulder area 62 is positioned over a shoulder of the user 12. In this embodiment, shoulder area 62 includes three shoulder accelerometers 60 which are operably mounted on a top area 64 over the top of the user's shoulder, on a deltoid muscle area 66 over the user's deltoid muscle adjacent the shoulder, and on a trapezius muscle area 68 over the user's trapezius muscle adjacent the shoulder.

The array of accelerometers 24 may also include an elbow accelerometer 70 mounted on an elbow area 72 of the flexible sleeve 22 adapted to be positioned over an elbow of the user 12. In one embodiment, one of the elbow accelerometers 70 may be operably mounted on a center elbow area 74 over the center area of the user's elbow, another is mounted on an ulna bone area 76 over the user's ulna bone adjacent the elbow, and a third elbow accelerometer 70 may be on a humerus bone area 78 over a user's humerus bone adjacent the elbow.

The array of accelerometers 24 may also include a wrist accelerometer 80 mounted on a wrist area 82 of the flexible sleeve 22, over or adjacent a user's wrist. In the embodiment of FIGS. 1 and 2, the wrist area 82 includes multiple wrist accelerometers 80, which may be operably mounted on a center wrist area 84 over the center of the user's wrist, on a radius bone area 86 over the user's radius bone adjacent the wrist, and an ulna bone area 88 over the ulna bone adjacent the user's wrist of the user's arm 14. In one embodiment, the wrist accelerometers 80 may further include a thumb area accelerometer 89 positioned on the distal end 38 of the flexible sleeve 22, adjacent the thumb 16 of the user.

As a result of this array of accelerometers 24, body movement data may be collected across a variety of locations as a means to best measure movement of the user's arm 14, for optimum treatment and rehabilitation of the user's injury. While FIGS. 1 and 2 illustrate one embodiment of the array of accelerometers 24, other arrangements of the accelerometers 24 may also be utilized, and such alternative arrangements that may be selected by one skilled in the art are therefore considered within the scope of the present invention.

The therapeutic sleeve device 10 may optionally include at least one gyroscope 90 operably mounted on the flexible sleeve 22 to work in conjunction with the array of accelerometers 24. The at least one gyroscope 90 may be utilized to measure the orientation of the flexible sleeve 22 while being worn by the user 12. However, the particular location of the at least one gyroscope 90 illustrated in FIGS. 1 and 2 may vary according to alternative embodiments devised by one skilled in the art. In the present embodiment, the gyroscope 90 is operably mounted on the shoulder area 62 of the flexible sleeve 22.

FIGS. 1 and 2 also illustrate a sensor glove 100 that may be worn over a user's hand to monitor hand movement and facilitate rehabilitation. The sensor glove 100 may have a first electrical connector 104 adapted to operably engage a second electrical connector 106 of the flexible sleeve 22. Such a connection allows an array of glove accelerometers 108 to become operably engaged with the data collection system 30. In the embodiment of FIGS. 1 and 2, an array of glove accelerometers 108 may be operably mounted to each joint on the fingers and thumb of the user's hand. It should be noted, however, that the number and location of the glove accelerometers 108 may vary according to the design of one skilled in the field.

Figure 3:
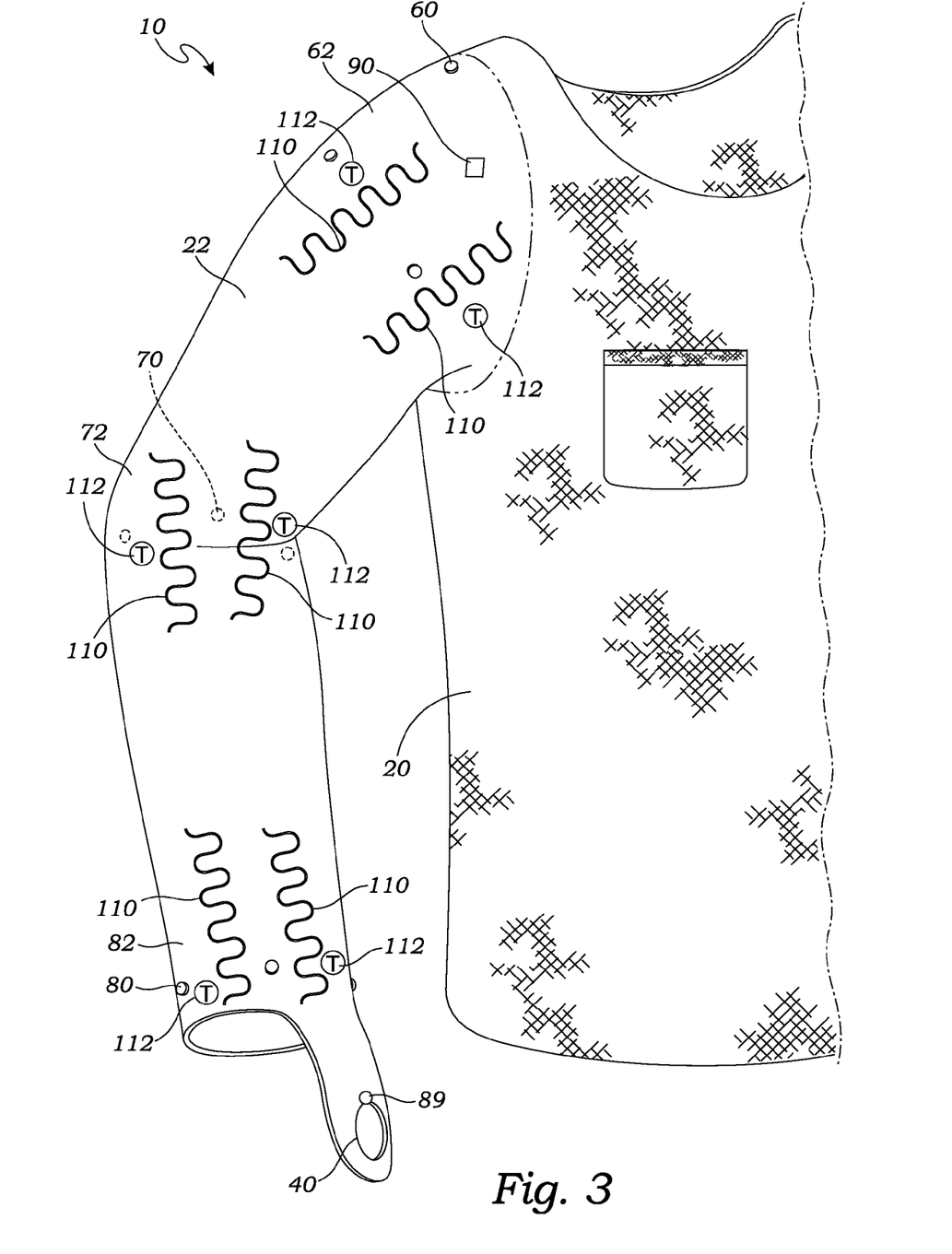
FIG. 3 is a perspective view of part of the therapeutic sleeve device, illustrating heating coils and temperature sensors operably mounted on a flexible sleeve of the therapeutic sleeve device.

FIG. 3 is a perspective view of the therapeutic sleeve device 10, illustrating heating coils 110 and temperature sensors 112 operably mounted on the flexible sleeve 22. In the embodiment of FIG. 3, the heating coils 110 apply heat as desired during rehabilitation exercises, to facilitate exercises and to avoid injury. The term "heating coil" is hereby defined to include any form of heating element that is known to those skilled in the art to apply therapeutic heat to the user wearing this form of therapeutic sleeve device 10, and the term should be broadly construed.

In the embodiment of FIG. 3, there are heating coils 110 positioned on the shoulder area 62, the elbow area 72, and the wrist area 82 of the flexible sleeve 22, for jointly or selectively applying heat to these areas during rehabilitation. The temperature sensors 112 are provided adjacent the heating coils 110 so that the temperature may be monitored and adjusted to ensure proper heating and to prevent burning the user. While one embodiment of the heating coils 110 is illustrated, other arrangements of the heating coils 110 or equivalent elements may also be utilized and should be considered within the scope of the present invention.

Figure 4:
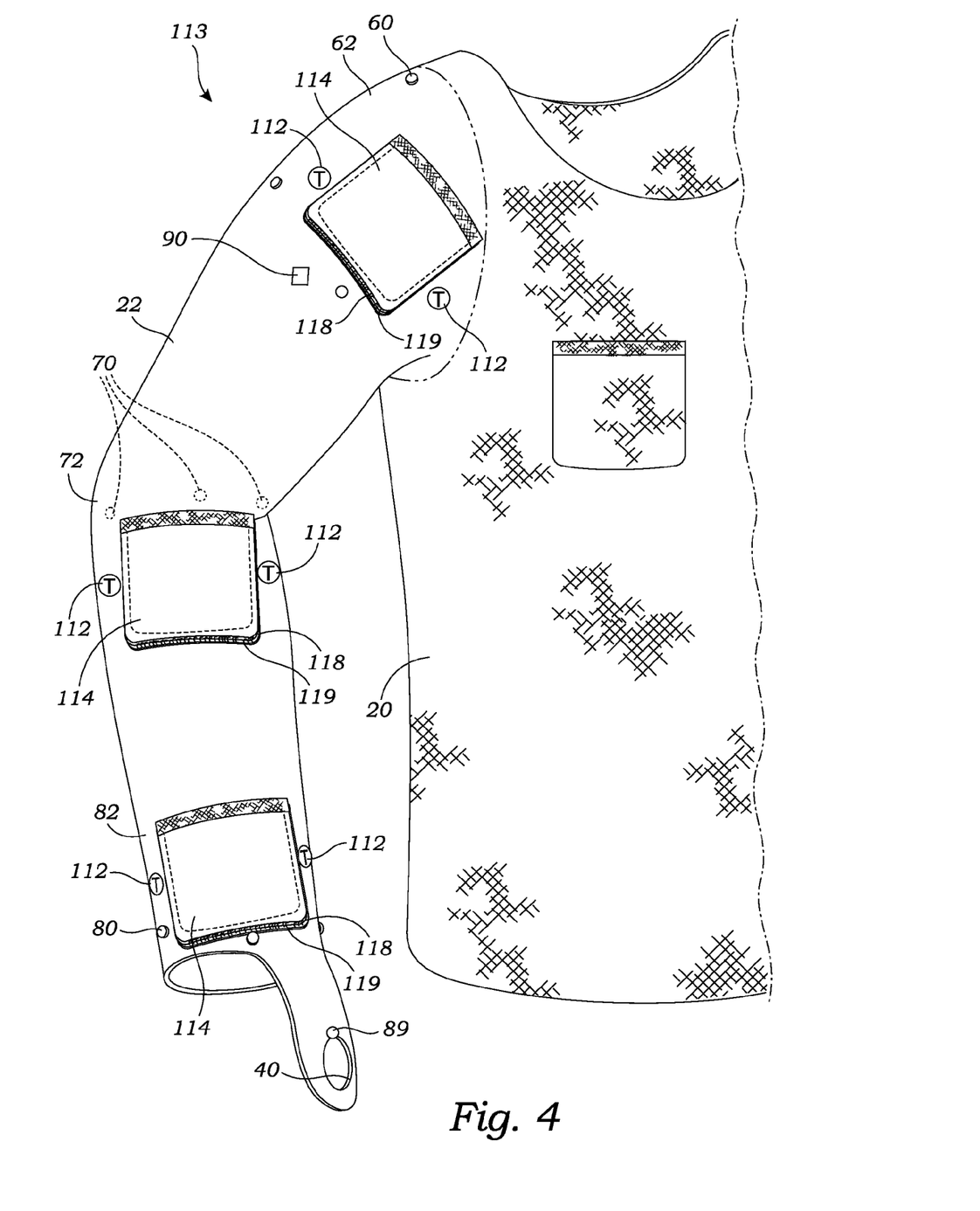
FIG. 4 is a perspective view of compartments formed on the flexible sleeve.
Figure 5:
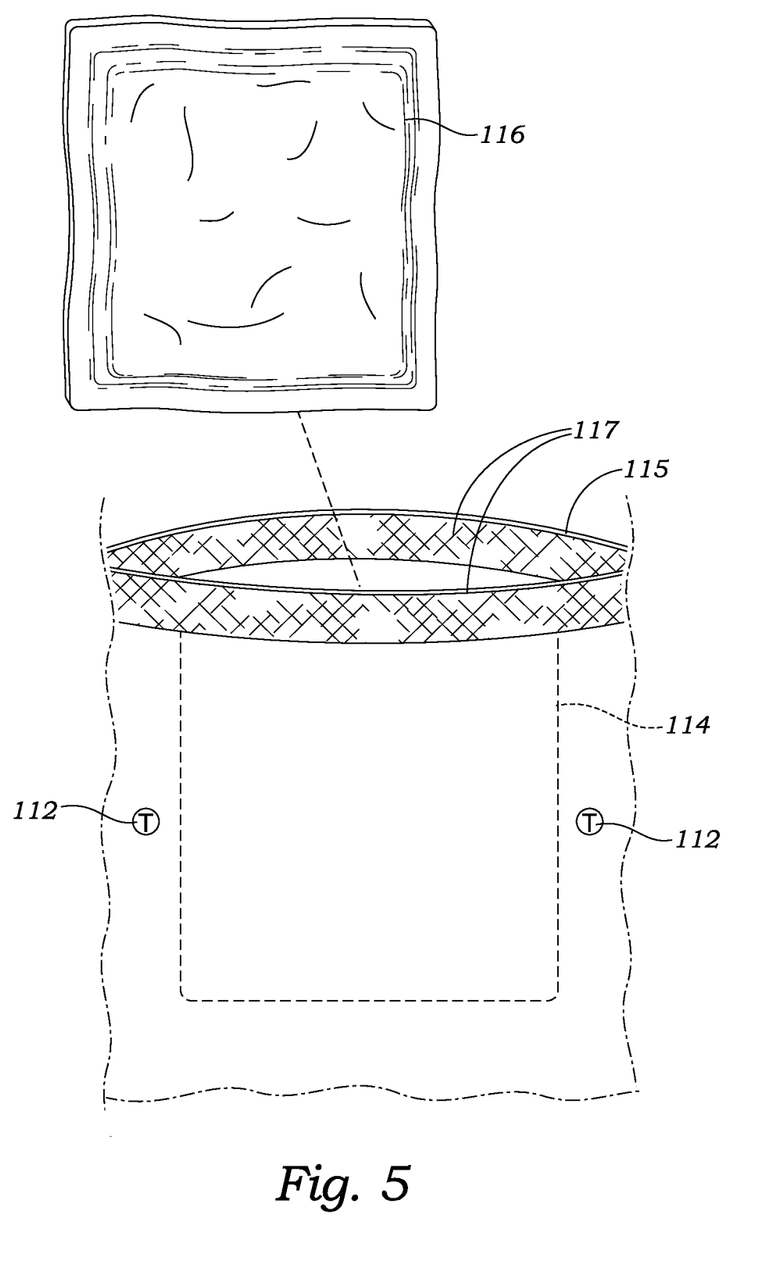
FIG. 5 is an exploded perspective view of a cold pack being inserted into one of the compartments of FIG. 4.

FIG. 4 is a perspective view of a cooling system 113 formed on the flexible sleeve 22 for selectively cooling the user's arm during rehabilitation, the cooling system of this embodiment including compartments 114. FIG. 5 is an exploded perspective view of one of the compartments 114, illustrating a cold pack 116 being positioned in the compartment 114. As illustrated in FIGS. 4 and 5, the compartment 114 may be formed in or on the flexible sleeve 22, and is adapted to receive and contain the cold pack 116 for cooling the arm of the user during rehabilitation exercises. The compartment 114 includes an opening 115 for receiving the cold pack 116, and the opening 115 may be removably closable with a compartment fastener 117 such as a hooks and loops fastener (e.g., VELCRO®), as illustrated, or other suitable fastener. In this embodiment, the temperature sensors 112 discussed above may also be used for monitoring the cooling of the user's arm, to ensure proper cooling is provided, and to make sure injury from overcooling does not occur.

In one embodiment, the compartment 114 may be removably attached to the flexible sleeve 22 with fasteners 118 and 119, such as a hooks and loops fasteners, or any other suitable fastener known in the field. Thus, the cold pack 116, having the fastener 118, may be operably mounted on the fastener 119 of the flexible sleeve 22 as a means to apply cold to the arm 14. An another alternative embodiment may be in which the compartment 114 is formed integrally with the flexible sleeve 22. The term "compartment" is hereby defined to broadly include any form of compartment, recess, or other mounting feature suitable for mounting the cold pack 116 on the flexible sleeve 22.

Figure 6:
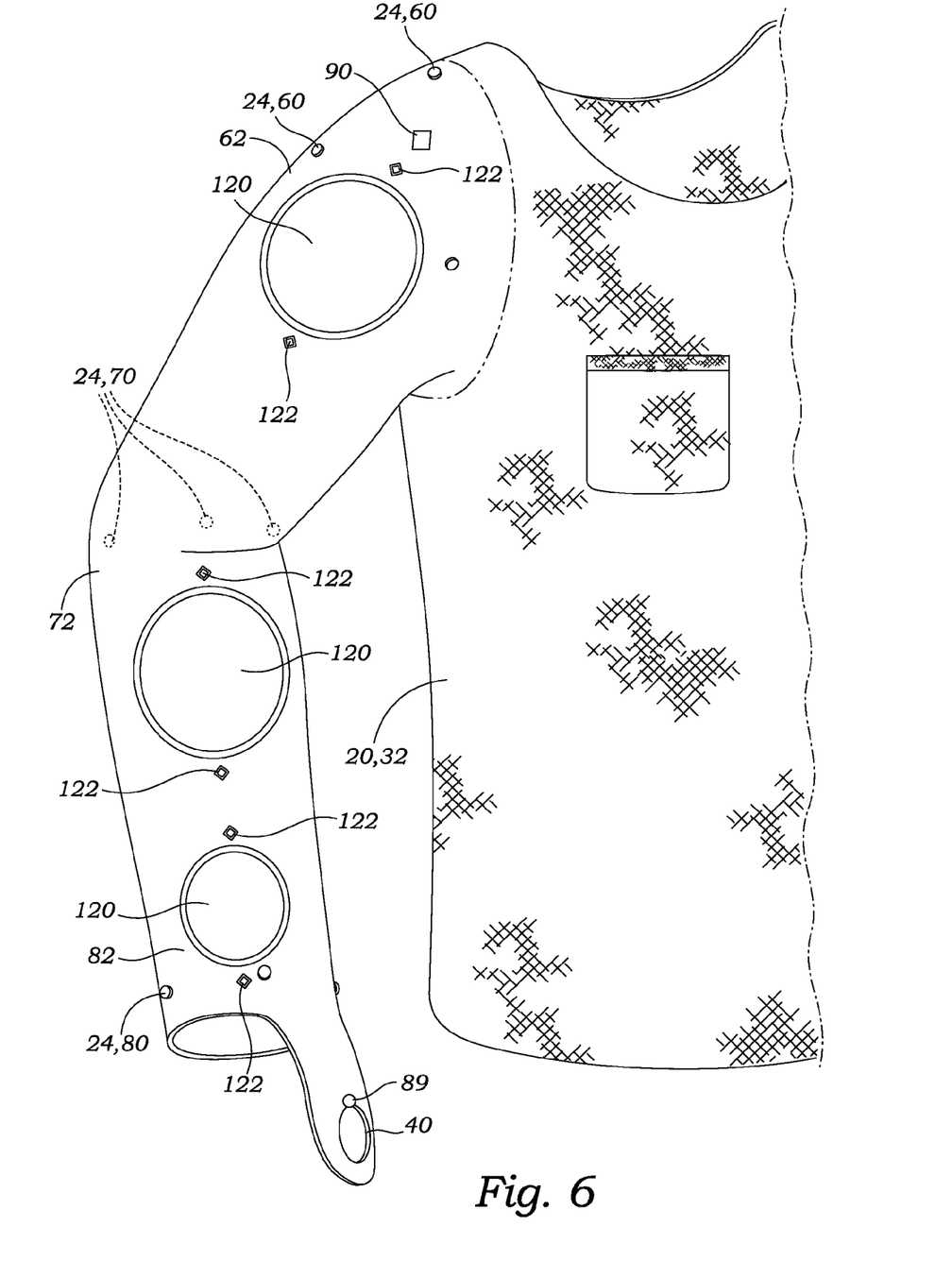
FIG. 6 is a perspective view of part of the therapeutic sleeve device, illustrating ultrasound treatment devices and electrical stimulation devices operably attached to the flexible sleeve.

The cold pack 116 may be utilized to alleviate joint pain, reduce inflammation, or achieve other therapeutic aims of those skilled in the art. The fasteners 119 of this embodiment are attached to the shoulder area 62, the elbow area 72, and the wrist area 82 of the flexible sleeve 22, so that the compartments 114 may be mounted over and/or adjacent each of the joints for optimal cooling where required; however, alternative placements may also be utilized, depending upon where the doctor or other treatment provider requires cooling FIG. 6 is a perspective view of the therapeutic sleeve device 10 in which ultrasound treatment devices 120 are operably attached to the shoulder area 62, elbow area 72, and wrist area 82 of the therapeutic sleeve device 10. The ultrasound treatment devices 120 may be attached to or integrated into the flexible sleeve 22 to provide physical therapy on the user's arm 14. The term "ultrasound treatment devices" is hereby defined to broadly include any form of device for directing ultrasonic or equivalent waves into the soft tissues of the user 12. In the present embodiment, the ultrasound treatment devices 120 may emit alternating compression and rarefaction of sound waves into the user's soft tissues, to be absorbed primarily by ligaments, tendons, scar tissues, and fasciae. Thus, the ultrasound treatment devices 120 may benefit the user 12 via thermal effects due to absorption of the sound waves, as well as non-thermal effects from cavitation. Cavitational effects result from the vibration of the user's tissue, which causes microscopic air bubbles to form and stimulate cell membranes to enhance cell-repair effects of the inflammatory response. Thus, the ultrasound treatment devices 120, coupled with the heating coils 110 and/or cold pack 116, may provide a mobile and effective means to repair injuries to the user 12.

Similarly, electrical stimulation contacts 122 may be operably attached to the shoulder area 62, elbow area 72, and wrist area 82 of the therapeutic sleeve device 10 to promote wound healing by utilizing pulsed electrical stimulation. The term "electric stimulation contacts" is hereby broadly defined to include any form of electrical contact for providing electrotherapy in which electrical stimulation is utilized to treat an injury.

In the present form of electrical stimulation therapy, the user undergoes repeated short treatments of electrical stimulation applied to the soft tissue of his or her arm. This electrical stimulation may be capable of delivering pulses at a predetermined pulse intensity and rate so as to treat the user remotely according to a range deemed appropriate by a physician. The electrical stimulation may be provided in conjunction with or in coordination with the rehabilitation exercises monitored by the system.

For example, a doctor or other person suitably skilled in the art may devise a treatment plan that includes certain exercises to be performed a certain number of times per day. The treatment may include therapeutic ultrasonic treatment and/or pulsed electrical stimulation before, during, or after each routine, according to a schedule devised by one skilled in the art. These therapies may be provided automatically by this system. When the system recognizes, via the accelerometers 24 and/or gyroscopes 90 and/or equivalent sensor, that the user is performing the exercises, it could automatically trigger coordinated ultrasonic therapy to coincide with the exercises. Then, once the exercises have stopped (or after a predetermined period), the system could then also initiate a routine of pulsed electrical stimulation. Such treatment regimes would be devised by skilled persons in the art, such as doctors, but they are enabled using the unique system of the present invention.

It is important to note that both the ultrasound treatment devices 120 and the electric stimulation contacts 122 of FIG. 6 may vary in form and placement according to one skilled in the field. For example, the therapeutic sleeve device 10 may or may not include both the ultrasound treatment devices 120 and the electric stimulation contacts 122, and/or the location of said elements may vary along the flexible sleeve 22. Alternative embodiments of the ultrasound treatment devices 120 and the electric stimulation contacts 122 are therefore considered within the scope of the present invention.

Figure 7:
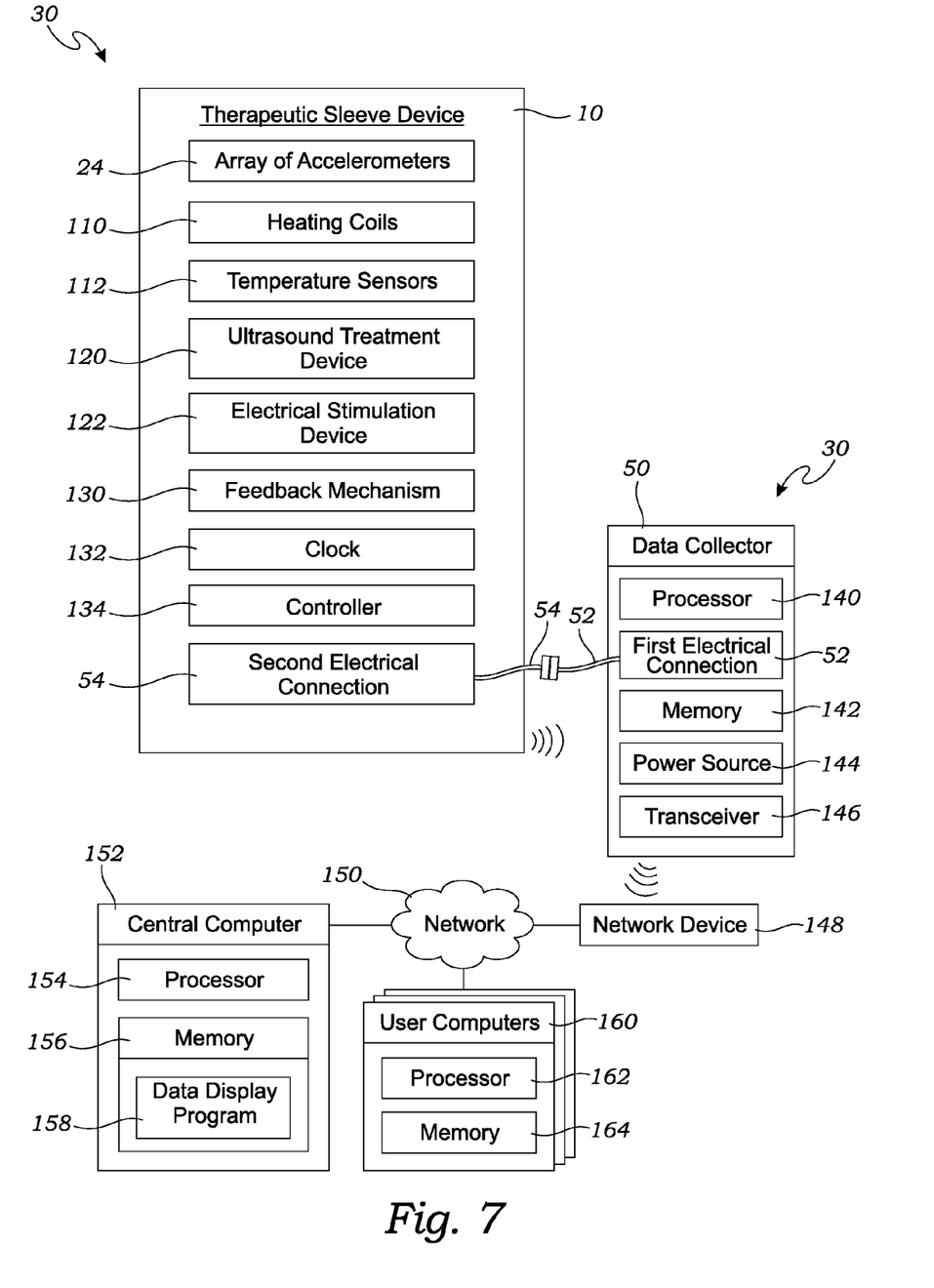
FIG. 7 is a block diagram of the therapeutic sleeve device and the data collector of FIG. 1.

FIG. 7 is a block diagram of the therapeutic sleeve device 10 and the data collector 50 of FIGS. 1 and 2. In this embodiment, the data collector 50 is positioned within pocket 46 of the shirt body 20 functions as part of one embodiment of the data collection system 30 for receiving data from the array of accelerometers 24.

As discussed above, the array of accelerometers 24 function to convert acceleration into an electrical signal, and provide digital output that reflects this activity, and this output may then be collected, transmitted, stored (e.g., to a computer), and analyzed. The therapeutic sleeve device 10 not only may provide immediate feedback to the user via a feedback mechanism 130 (e.g., audible alert or instructions, visual flashing, data display, etc.), it also transmits the data to the data collection system 30 for storage and analysis. The user may be any individual whose movement requires close tracking, such as a medical patient in rehabilitation, an athlete (in training, therapy, etc.), or other person, such as an employee or person working in a remote environment. Those skilled in the art may devise a wide range of uses of this system, and such alternatives should be considered within the scope of the present invention.

In the embodiment of FIG. 7, the therapeutic sleeve device 10 includes a clock 132 to enable the system to track movement as a function of time, and to determine when certain actions should be taken, when certain therapies should be applied, and for how long they should continue. As a result, the clock 132 may provide a "time-stamp" for particular treatments, thus providing a physician with confirmation that a desired therapy has been completed. The construction and function of the clock 122 are well known in the art, and are therefore not discussed in greater detail.

The therapeutic sleeve device 10 also may include a controller 134 or other form of processor and/or memory suitable for governing the operation of the therapeutic sleeve device 10. The controller 134 may be configured to receive data from the array of accelerometers 24, the temperature sensors 112, and any other sensors, and to also operatively control the ultrasound treatment devices 120, and/or the electrical stimulation contacts 122, and may also process that data into a storable format. The data may be stored in a local memory if desired, but in the illustrated embodiment the data is transmitted via the first and second electrical connections 52 and 54 (or via alternative methods, e.g., wireless transmission) to the data collector 50 for later retrieval and analysis. Since the controller 134 structure and function are known to those skilled in the art, it is not described in greater detail herein.

In the embodiment of FIG. 7, the data collection system 30 includes the data collector 50 that houses a processor 140 and a memory 142. The processor 140 and the memory 142 may be configured to receive and store data from the therapeutic sleeve device 10, and to also operatively control the operation of the therapeutic sleeve device 10. The data may be stored in the memory 142 for later retrieval and analysis, or it may be immediately transmitted to a central computer 152 for further processing and distribution, as discussed in greater detail below.

In this embodiment, the therapeutic sleeve device 10 does not have a power source itself (although it may in alternative embodiments), but the data collector 50 includes a power source 144 for providing power to the various components and devices described herein. The power source 144 may be any suitable source of power, such as, e.g., batteries operatively installed in the data collector 50.

In the embodiment of FIG. 7, the data collector 50 may include a transceiver 146 for transmitting the data to a wireless network device 148 to be accessed by the central computer 152 (or any other computer device desired) via a network 150 (e.g., the Internet, or other suitable network). The term "transceiver" is hereby defined to include any device that is known to those skilled in the art for transmitting the data to an outside receiver, and the term should be broadly construed. While a wireless connection is illustrated herein, alternative connections may also be used. For example, the data collector 50 could also be periodically connected (i.e., docked) with a docking station for uploading the data to the central computer 152.

The central computer 152 may include a processor 154 and a memory 156. The memory 156 may not only store the data downloaded from the data collector 50 (and, presumably, from a large number of additional users), it also may include a data display program 158 for analyzing the data to determine whether the user is using the therapeutic sleeve device 10 properly, and complying with instructions (e.g., complying with rehabilitation instructions, and performing the rehab exercises properly). The data display program 158 may function to output the data in a manner that enables easy analysis, and assistance in correcting any errors, and accommodating any special needs or requirements.

The central computer 152 may enable various persons may then access this information via the network 150 to analyze movement data, use of the therapeutic sleeve device 10, and also operation of the therapeutic sleeve device 10. The access may be direct from the central computer 152, or via user computers 160 (e.g., a personal computer) that also include a processor 162 and a memory 164 as is well known in the art.

Potential persons who may monitor the data include a patient performing physical rehabilitation (checking his or her own progress), a physical trainer overseeing the physical rehabilitation, a physician monitoring the patient's treatment, and also potentially electronic monitors that take electronic action in response to the data. For example, if the movement data suggests errors in the physical rehabilitation exercises, an electronic monitor (e.g., a program on a computer or similar electronic device) might alert the patient and/or his trainer and/or physician, and/or it might take other action, such as emailing the patient a video showing him or her how to perform the exercise more correctly, and/or reminding him or her to do the exercises (if they are not being performed on the correct schedule). The term "user interface" is intended to encompass all of these options, and include any form of monitoring that may be desired by one skilled in the art.

As the present discussion demonstrates, the information on the central computer 152 may be accessed by any suitable individual (e.g. doctor, physical therapist, employer, etc) who seeks to analyze the collected data. Furthermore, the central computer 152 may be in a variety of forms, such as a cellular telephone, a laptop computer, a personal computer, a personal digital assistant (PDA), or any other suitable device known in the art. Therefore, while FIG. 8 illustrates one embodiment of the data collection system 30, other arrangements of computers or computer devices may also be utilized according to what is deemed appropriate by one skilled in the art.

Figure 8:
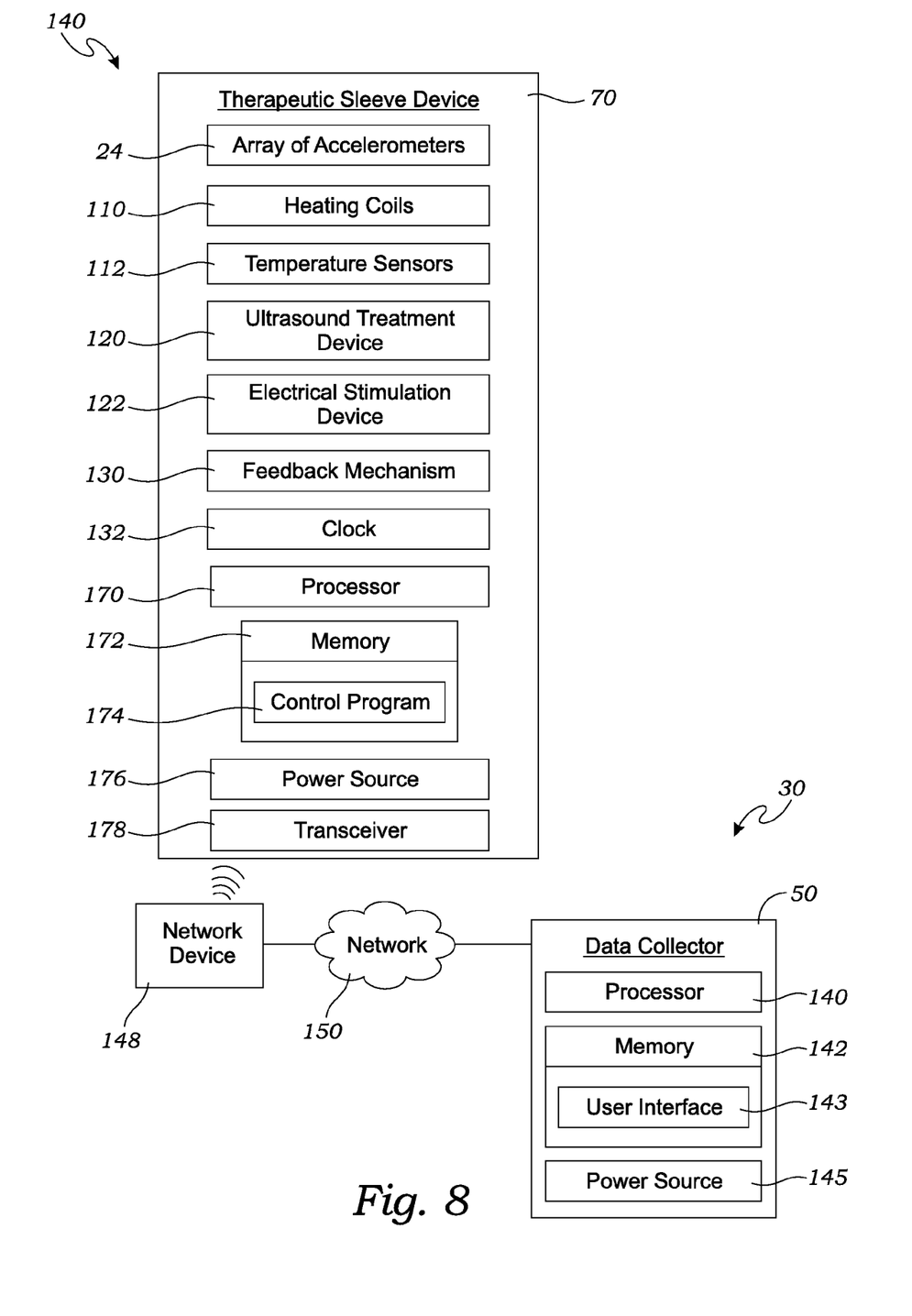
FIG. 8 is a block diagram of the therapeutic sleeve device and a second embodiment of the data collection system.

FIG. 8 is a block diagram of a second embodiment of a therapeutic sleeve device 70 adapted for use with another embodiment of the data collection system 30. In this embodiment, the data collection system 30 is located remotely, and is operably engaged with the therapeutic sleeve device 70 via the network device 148 and the network 150.

In this embodiment, the therapeutic sleeve device 70 includes a processor 170 and a memory 172 so that data can be collected and stored locally in case there is a loss of wireless connection. The memory 172 may include a control program 174 for controlling the operation of the therapeutic sleeve device 70. Furthermore, since there is no wired connection, the therapeutic sleeve device 70 may include a power source 176, and a transceiver 178 for wireless communication with the data collector 50.

In this embodiment, the data collector 50 may include a user interface 143 that enables the remote control of the therapeutic sleeve device 70. The user interface 143 may include a browser or similar program, and/or a proprietary program, that is intended to enable the operative control and oversight of a large number of the therapeutic sleeve devices 70, and may also include, generally, a wide range of computing devices used by a wide range of potential data users.

As used in this application, the terms computer, processor, memory, and other computer related components, are hereby expressly defined to include any arrangement of computer(s), processor (s), memory device or devices, and/or computer components, either as a single unit or operably connected and/or networked across multiple computers (or distributed computer components), to perform the functions described herein.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application.

What is claimed is:

1. A diagnostic sleeve device for tracking and recording movement data of an arm of a user, the diagnostic sleeve device comprising:
    a flexible compression sleeve shaped to be worn around the arm of the user;
    an array of accelerometers disposed on or within the flexible sleeve to physically associate with positions on the arm of the user, each of the array of accelerometers having a sample rate that can be configured for sensing body movement during a movement activity;
    a power source operably connected to the array of accelerometers; and
    a data collection system operably connected to the array of accelerometers, the data collection system being adapted for receiving data from the array of accelerometers and processing that data into a storable format.

2. The diagnostic sleeve device of claim 1, wherein the array of accelerometers comprises:
    at least two shoulder accelerometers that are mounted in a shoulder area of the flexible sleeve adapted to be positioned over a shoulder of the user;
    at least two elbow accelerometers that are mounted in an elbow area of the flexible sleeve adapted to be positioned over an elbow of the user; and
    at least two wrist accelerometers that are mounted in a wrist area of the flexible sleeve over or adjacent a wrist of the user.

3. The diagnostic sleeve device of claim 2, wherein the at least two shoulder accelerometers include one accelerometer mounted on a deltoid muscle area of the flexible sleeve over the user's deltoid muscle adjacent the shoulder, and a second accelerometer mounted on a trapezius muscle area over the user's trapezius muscle adjacent the shoulder.

4. The diagnostic sleeve device of claim 2, wherein the at least two elbow accelerometers include three accelerometers, one of the elbow accelerometers being operably mounted on a center elbow area of the flexible sleeve over the center area of the user's elbow, another being mounted on an ulna bone area of the flexible sleeve over the user's ulna bone adjacent the elbow, and another being mounted on a humerus bone area of the flexible sleeve over a user's humerus bone adjacent the elbow.

5. The diagnostic sleeve device of claim 2, wherein the at least two accelerometers include three accelerometers positioned adjacent the wrist of the user, in which one of the accelerometers is operably mounted over the radius area adjacent the wrist, another is mounted over the ulna area adjacent the wrist, and a third is positioned on the flexible sleeve between the user's thumb and index finger.

6. The diagnostic sleeve device of claim 1, further comprising:
    at least one heating coil operably positioned within the flexible sleeve for delivering heat to the arm of the user; and
    at least one temperature sensor operably mounted on the flexible sleeve adjacent the heating coils for monitoring the temperature of the diagnostic sleeve device.

7. The diagnostic sleeve device of claim 1, wherein the data collection system includes a data collector operably connected to the array of accelerometers, the data collector having a processor and a memory configured to receive data from the array of accelerometers and process that data into a storable format.

8. The diagnostic sleeve device of claim 1, wherein the data collection system includes a transceiver and a data collector having a processor and a memory, wherein the array of accelerometers is operably connected with the transceiver for transmitting data from the array of accelerometers to the data collector for processing and storage.

9. The diagnostic sleeve device of claim 1, wherein data collection system includes a data collector operably connected to the plurality of accelerometers via a transceiver, and further includes a central computer operably connected to the data collector via a network, the central computer comprising a processor and a memory operably connected with the processor for receiving data from the data collector and configured to process the data into a storable format.

10. The diagnostic sleeve device of claim 1, further comprising at least one gyroscope operably mounted on the flexible sleeve adjacent to the array of accelerometers for measuring an orientation of the flexible sleeve while being worn by the user.

11. The diagnostic sleeve device of claim 1, further comprising therapeutic ultrasound transducers operably mounted on the flexible sleeve and operably controlled for delivering ultrasonic therapy to the arm of the user in coordination with physical therapy monitored by the array of accelerometers.

12. The diagnostic sleeve device of claim 1, further comprising a compartment formed in or on the flexible sleeve, and a cold pack shaped to fit within the compartment for cooling the arm of the user when operably positioned within the compartment.

13. The diagnostic sleeve device of claim 1, wherein the flexible sleeve is a compression sleeve.

14. The diagnostic sleeve device of claim 1, further comprising a sensor glove having a first electrical connector adapted to operably engage a second electrical connector of the flexible sleeve for operably engaging an array of glove accelerometers with the data collection system.

15. A diagnostic shirt comprising:
   a shirt body for covering an abdomen of a user, and two compression sleeves shaped to be worn over the upper extremities of the user;
   an array of accelerometers disposed on or within each of the compression sleeves to physically associate with positions on the upper extremities of the user, each of the array of accelerometers having a sample rate that can be configured for sensing body movement during a movement activity;
   a power source operably connected to the array of accelerometers; and
   a data collection system operably connected to the array of accelerometers, the data collection system having a means for receiving data from the array of accelerometers and processing that data into a storable format.

16. The diagnostic shirt of claim 15, wherein the shirt body is constructed of a flexible, elastic, lightweight fabric that conforms to the user and does not compress or constrict; and wherein the compression sleeves are form-fitting and compress the arm of the user.

17. The diagnostic shirt of claim 16, further comprising:
   a pocket on the shirt body;
   a data collector of the data collection system operably positioned within the pocket;
   a first electrical connection electrically connected with the array of accelerometers; and
   a second electrical connection of the data collector that is removably connected with the first electrical connection, for allowing the array of accelerometers to transmit data to the data collector.

* * * * *